United States Patent [19]

Berger

[11] 4,070,467

[45] Jan. 24, 1978

[54] TRANS-OCTAHYDRO-PYRIDO-INDOLO-BENZAZEPINE-3-ALKANOLS, -ALKANONITRILES,-ALKANOIC ACID AND ESTER AS TRANQUILIZERS

[75] Inventor: Joel G. Berger, Freeport, N.Y.

[73] Assignee: Endo Laboratories, Inc., Garden City, N.Y.

[21] Appl. No.: 675,113

[22] Filed: Apr. 8, 1976

[51] Int. Cl.² .................... C07D 471/14; A61K 31/55
[52] U.S. Cl. ................................ 424/256; 260/293.55
[58] Field of Search .................... 260/293.55; 424/256

[56] References Cited

U.S. PATENT DOCUMENTS

| 3,932,650 | 1/1976 | Adams | 260/239.55 |
| 3,983,123 | 9/1976 | Adams | 260/293.55 |

Primary Examiner—Cecilia M. S. Jaisle

[57] ABSTRACT

Certain 3-substituted trans-octahydro-pyrido-pyrrolo-benzazepines are useful as major tranquilizers in warm-blooded animals or are useful as intermediates for producing such major tranquilizers.

27 Claims, No Drawings

TRANS-OCTAHYDRO-PYRIDO-INDOLO-BENZAZEPINE-3-ALKANOLS, -ALKANONITRILES,-ALKANOIC ACID AND ESTER AS TRANQUILIZERS

BACKGROUND OF THE INVENTION

U.S. Pat. No. 3,890,327, granted to Joel Berger on June 17, 1975, discloses the compound trans-1,2,2,3,4,4a,8,9,14a-octahydropyrido[4', 3':2,3]indolo[1,7-ab][1]benzazepine:

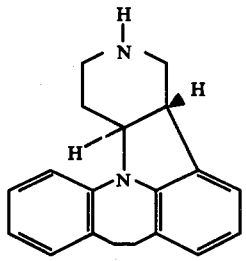

(I)

and its use as an analgesic. This compound is a convenient starting material for virtually all of the compounds from within the scope of the present invention.

Copending U.S. patent application Ser. No. 596,851, filed July 17, 1975, now U.S. Pat. No. 4,018,930, issued Apr. 19, 1977 by Joel G. Berger, (which is a continuation-in-part of U.S. patent application Ser. No. 422,615, filed Dec. 6, 1973 and now abandoned) discloses certain novel indolobenzazepines of the general formula:

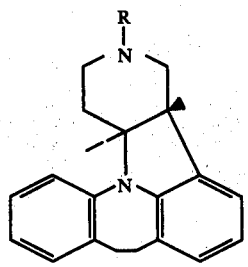

(II)

and their pharmaceutically suitable acid addition salts, where R is certain organic radicals, which indolobenzazepines are useful as analgesics and sedative-tranquilizers. In particular, U.S. Ser. No. 596,851 discloses compounds of formula II where R is, among other things, a $C_3$–$C_8$ oxoalkyl side chain.

U.S. Pat. No. 3,932,650, granted to Charles Adams on Jan. 13, 1976 (which is a continuation-in-part of U.S. patent application Ser. No, 325,352, filed Jan. 22, 1973 and now abandoned) discloses certain other compounds of formula II above wherein R is certain other organic radicals.

Finally, U.S. Pat. Nos. 3,373,168 and 3,457,271 disclose certain compounds of the formula:

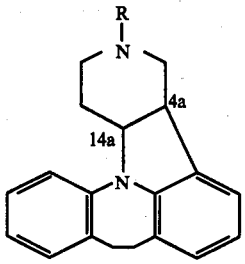

(III)

wherein R is alkyl of 1 to 7 carbon atoms and the compounds have the cis configuration of the 4a and 14a hydrogens. These compounds are disclosed as antidepressants.

SUMMARY OF THE INVENTION

This invention relates to a class of novel compounds of the following formula:

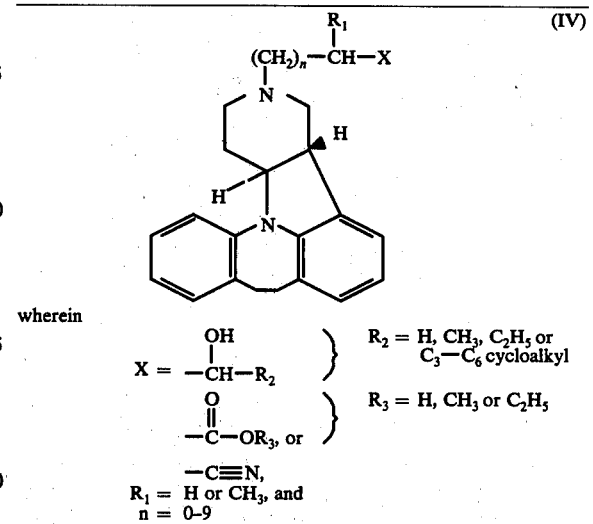

wherein $$X = -\underset{\underset{R_2}{|}}{\overset{\overset{OH}{|}}{C}}H-R_2$$

$R_2$ = H, CH$_3$, C$_2$H$_5$ or C$_3$–C$_6$ cycloalkyl $$-\overset{O}{\underset{||}{C}}-OR_3, \text{ or}$$

$R_3$ = H, CH$_3$ or C$_2$H$_5$ $-C{\equiv}N$, $R_1$ = H or CH$_3$, and
n = 0–9 provided that when $R_1$ = CH$_3$, n = 1.

provided that when $R_1$ = CH$_3$, n = 1.

The compounds of formula II are useful as CNS depressants with major tranquilizer activity or intermediates for producing such major tranquilizers. That is, for a given compound, even though one of the two antipodes may not be useful as a tranquilizer per se, it would be useful for making the other antipode.

Presently preferred compounds from within this scope include those where:

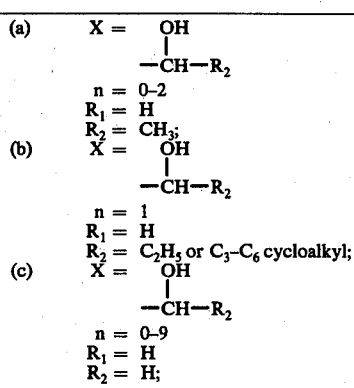

(d) X = OH
         |
        —CH—R$_2$
    n = 1
    R$_1$ = CH$_3$
    R$_2$ = H;
(e) X = —C≡N
    n = 0-9
    R$_1$ = H;
(f) X = —C≡N
    n = 1
    R$_1$ = CH$_3$;
(g) X = O
        ‖
       —C—OR$_3$
    n = 0-9
    R$_1$ = H
    R$_3$ = H, CH$_3$ or C$_2$H$_5$; and
(h) X = O
        ‖
       —C—OR$_3$
    n = 1
    R$_1$ = CH$_3$
    R$_3$ = H, CH$_3$ or C$_2$H$_5$.

The present invention also includes pharmaceutical compositions comprising a pharmaceutically suitable carrier and an effective amount of a compound of formula IV, and a method for producing a tranquilizing effect in warm-blooded animals comprising administering an effective amount of a compound of formula IV. The invention also includes a processes for making the compounds of formula IV as described hereafter.

DETAILED DESCRIPTION OF THE INVENTION

Synthesis of the Final Product Compounds

Each of the compounds of formula IV can be made by one or more of the methods outlined below:

1. The compounds of formula IV wherein:

n = 1;
          O
          ‖
X = —C—OR$_3$, or —C≡N; and
R$_3$ = CH$_3$ or C$_2$H$_5$ can be made as follows:

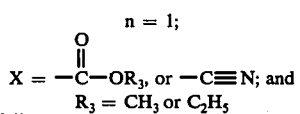

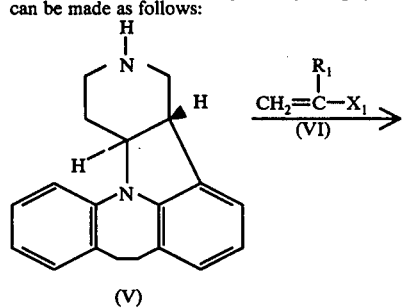

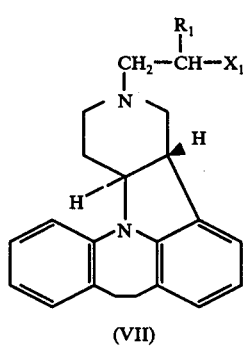

R$_1$ is as previously defined, and

X$_1$ is those values of X listed immediately above.

The reaction outlined immediately above can be conveniently carried out in a lower alkanol (such as methanol or ethanol), in an ether (such as diethyl ether, tetrahydrofuran or 1,4-dioxane), or in chloroform at temperatures of from 20°–101° C for about 1 to 3 days.

2. The compounds of formula IV wherein:

n = 0-9;
       OH            O
       |             ‖
X = —CH—R$_2$, —C—OR$_3$, or —C≡N;
R$_2$ = H, CH$_3$, C$_2$H$_5$ or C$_3$-C$_6$ cycloalkyl; and
R$_3$ = CH$_3$ or C$_2$H$_5$ can be made as follows:

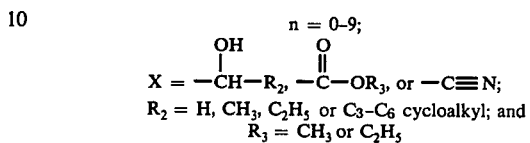

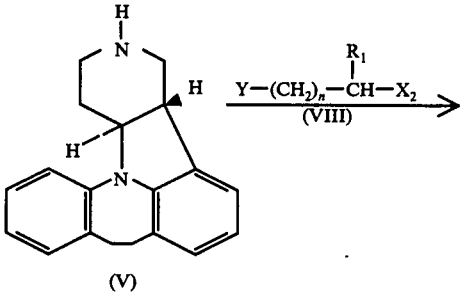

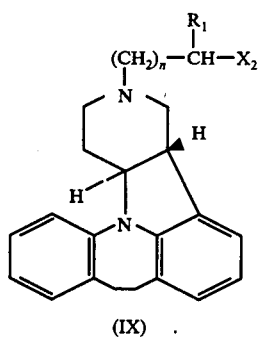

R$_1$ is as previously defined;
X$_2$ is those values of X listed immediately above; and
Y is chlorine, bromine or iodine.

This reaction is most advantageously carried out in a highly polar, aprotic solvent (such as N,N-dimethylformamide (DMF), N,N-dimethylacetamide (DMAC) or hexamethylphosphoric triamide (HMPT)) at temperatures of 60°–80° C. in the presence of an acid acceptor such as triethylamine, powdered sodium carbonate, sodium bicarbonate, potassium carbonate or potassium bicarbonate.

When Y is chlorine or bromine, the addition of potassium iodide to the reaction mixture will promote the reaction. When n is 1, and X$_2$ is

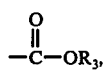

or —C≡N, method (1), above, is preferred.

3. The compounds of formula IV wherein:

n = 0-9;
       OH
       |
X = —CH—R$_2$; and
R$_2$ = H, CH$_3$, C$_2$H$_5$ and C$_3$-C$_6$ cycloalkyl
can be made as follows:

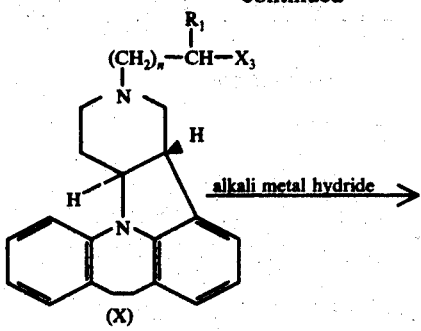

(X)

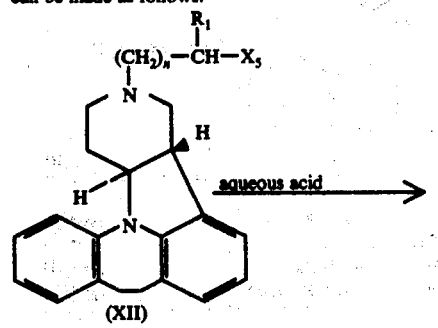

(XI)

$R_1$ is as previously defined;

$X_3$ is $-\overset{O}{\underset{\|}{C}}-OR_3$ or $-\overset{O}{\underset{\|}{C}}-R_4$;

$R_3$ is $CH_3$ or $C_2H_5$; and $R_4$ is H, $CH_3$, $C_2H_5$ or $C_3$-$C_6$ cycloalkyl;

$X_4$ is $-\overset{OH}{\underset{|}{CH}}-R_2$ $R_2$ is H, $CH_3$, $C_2H_5$ or $C_3$-$C_6$ cycloalkyl;
provided that when $X_3$ is $-\overset{O}{\underset{\|}{C}}-R_4$, $R_2 = R_4$; and when $X_3$ is $-\overset{O}{\underset{\|}{C}}-OR_3$, $R_2 = H$.

The reduction shown above is carried out with an alkali metal complex hydride of boron or aluminum in a suitable solvent (such as $NaBH_4$ or $LiBH_4$ in a lower alkanol such as methanol or ethanol, at 20°–30° C.; $LiAlH_4$ in diethyl ether or tetrahydrofuran (THF) at 35°–65° C.; or $NaAlH_2(OCH_2CH_2OCH_3)_2$ in benzene or toluene at 20°–110° C.).

4. The compounds of formula IV wherein n = 0–9;

$X = -\overset{O}{\underset{\|}{C}}-OR_3$; and $R_3 = H$, can be made as follows:

(XII)

(XIII)

$R_1$ is as previously defined;

$X_5$ is $-\overset{O}{\underset{\|}{C}}-OR_3$ and $R_3$ is $CH_3$ or $C_2H_5$.

The hydrolysis shown above is carried out by refluxing for 15–60 minutes in an aqueous mineral acid (such as 6N HCl) leading to convenient isolation of the product as its mineral acid salt.

Synthesis of the Starting Material Compound

As indicated above, the starting material compound of formula V is the subject of U.S. Pat. No. 3,890,327. Its synthesis is described in detail therein, and such synthesis description as it appears from column 2, line 63 through column 7, line 21 is hereby incorporated by reference.

The compound of formula V has two assymetric centers resulting from the reduction of the $\Delta^{4a,14a}$ to the trans-fused system. This compound can be separated into its dextro- and levo-rotatory enantiomers, which serve as starting materials for the optically active compounds of the present invention. Its separation has been carried out as follows:

EXAMPLE 1

17.7 grams of (±)-trans-1,2,3,4,4a,8,9,14a-octahydropyrido[4',3':2,3]indolo[1,7-ab][1]benzazepine and 23 grams of (−)-dibenzoyltartaric acid were dissolved in 800 ml of boiling ethanol and allowed to slowly cool to room temperature. The crystalline salt obtained was filtered and converted to the free base. This gummy product was recrystallized twice from ethanol and the head fractions discarded. The mother liquors were concentrated and treated with ethanolic HCl and acetone to give a hydrochloride salt. This material was reconverted to base, treated with an equivalent amount of dibenzoyltartaric acid in ethanol, and the salt was allowed to slowly crystallize. This was then reconverted to the free base and then to the hydrochloride prepared by treatment with ethanolic HCl, $[\alpha]_D^{25} = -231.5°$ (c 0.30, $CH_3OH$).

The mother liquors obtained from the initial tartrate were concentrated to 150 ml; some solids were filtered off, and the filtrates were further concentrated to dryness. The residue was converted to the free base which was then recrystallized twice from ethanol in each case discarding solid head fractions and retaining mother liquors. The second mother liquor was treated with an ethanolic HCl, and the solvent was evaporated leaving a gum which was recrystallized from acetone to give the hydrochloride salt, $[\alpha]_D^{25} = +230.0°$ (c 0.38, $CH_3OH$).

The following examples illustrate the preparation of the compounds of this invention.

EXAMPLE 2

(±)-trans-1,2,3,4,4a,8,9,14a-octahydropyrido[4',3':2,3]-indolo[1,7-ab][1]benzazepine-3-propionic acid, ethyl ester Six ml (0.054 moles) of ethyl acrylate was added to 11 grams (0.040 moles) of the compound of formula V dissolved in 300 ml of ethanol. The mixture was left standing at room temperature for 2.5 days. The resulting precipitate was filtered and recrystallized from ethanol yielding the title compound, m.p. 111.8° C.

|  | % C | % H | % N |
|---|---|---|---|
| cal'd: | 76.55 | 7.51 | 7.44 |
| found: | 76.59 | 7.46 | 7.49 |

The following compounds can be made in a manner similar to that described in Example 2, above:

TABLE 1

(IV) (n = 1)

| | X | $R_1$ | m.p. | (salt) |
|---|---|---|---|---|
| a. | —C≡N | —H | 162.5-162.9° | — |
| b. | —C≡N | —CH$_3$ | | |
| c. | —COOCH$_3$ | —H | 220-221° (dec.) | (HCl) |
| d. | —COOCH$_3$ | —CH$_3$ | 130-132° | — |

EXAMPLE 3

(±)-trans-1,2,3,4,4a,8,9,14a-octahydropyrido[4'3':2,3]-indolo[1,7-ab][1]benzazepine-3-butyric acid, ethyl ester 7.2 grams (0.044 moles) of potassium iodide, 12.6 ml (0.090 moles) of triethylamine, and 6.6 grams (0.044 moles) of ethyl 4-chlorobutyrate were added to a solution of 11 grams (0.040 moles) of the compound of the formula V dissolved in 100 ml of dimethylformamide. The mixture was heated at about 60° C for 24 hours and was then poured into water and extracted with benzene. The organic phase was washed with a saturated solution of sodium chloride and then evaporated in vacuo to dryness. Trituration with ethanol yielded a solid which was dissolved in benzene and chromatographed through basic alumina using benzene as the eluant. The benzene was evaporated and the resulting solid was recrystallized from ethanol, yielding the title compound, m.p. 208°-208.5° C.

|  | % C | % H | % N |
|---|---|---|---|
| cal'd: | 76.89 | 7.74 | 7.17 |
| found: | 77.01 | 7.73 | 7.10 |

By using the appropriate functionalized halo compound and the compound of formula V, the following compounds can be prepared in a manner similar to that described in Example 3, above:

TABLE 2

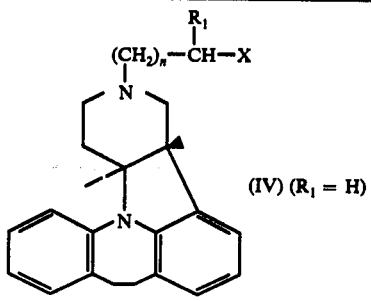

(IV) ($R_1$ = H)

| | n | —X | m.p. | (salt) |
|---|---|---|---|---|
| a. | 0 | —C≡N | | |
| b. | 2 | —C≡N | 134-135.5° | — |
| c. | 4 | —C≡N | | |
| d. | 0 | —COOC$_2$H$_5$ | | |
| e. | 1 | —COOC$_2$H$_5$ | 111.8° | |
| f. | 3 | —COOC$_2$H$_5$ | 256-258° | (HCl) |
| g. | 4 | —COOC$_2$H$_5$ | 198-199 | (HCl) |
| h. | 9 | —COOC$_2$H$_5$ | | |

EXAMPLE 4

(±)-trans-1,2,3,4,4a,8,9,14a-octahydropyrido[4',3':2,3]-indolo[1,7-ab][1]benzazepine-3-butyric acid, hydrochloride Five grams (0.013 moles) of the title compound in Example 3, above, was suspended in 50 ml of dioxane and 75 ml of 3.5 N hydrochloric acid and was refluxed for 7 hours. The reaction mixture was then evaporated to dryness in vacuo and the resulting product was recrystallized from acetone, yielding the title compound, m.p. 275° C (dec.).

|  | % C | % H | % N | % Cl |
|---|---|---|---|---|
| cal'd: | 69.24 | 6.84 | 7.02 | 8.86 |
| found: | 68.66 | 6.84 | 7.11 | 9.26 |

Using an appropriate methyl or ethyl ester, the following acid addition salts can be prepared in a manner similar to that described in Example 4, above:

TABLE 3

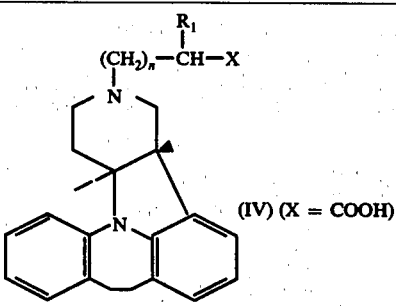

(IV) (X = COOH)

| | n | $R_1$ | m.p. | (Salt) |
|---|---|---|---|---|
| a. | 0 | —H | | |
| b. | 1 | —H | 281-282° (dec.) | (HCl) |
| c. | 1 | —CH$_3$ | 231-232° (dec.) | (HCl) |
| d. | 3 | —H | 300° (dec.) | (HCl) |
| e. | 4 | —H | 284-286° (dec.) | (HCl) |

EXAMPLE 5

(±)-trans-1,2,3,4,4a,8,9,14a-octahydro-α-methyl-pyrido[4',3':2,3]indolo[1,7-ab][1]benzazepine-3-butanol, hydro-chloride One gram (0.027 moles) of sodium borohydride was added in one portion to 0.091 moles of the ketone (±)-5-(trans-1,2,3,4,4a,8,9,14a-octahydropyrido[4',3':2,3]indolo[1,7-ab][1]benzazepin-3-yl)-2-pentanone dissolved in 100 ml of absolute ethanol. The reaction mixture was left stirring at room temperature for 2.5 hours and was then decomposed with 2.5 N hydrochloric acid. The reaction mixture was then made basic with sodium hydroxide, and the ethanol was evaporated in vacuo. Additional water was added, and the yellow residue was extracted with methylene chloride. The organic phase was washed with water, dried with sodium sulfate, filtered, and evaporated in vacuo. The residue was taken up in dry ether and etheral hydrochloric acid was then added. The precipitate was then filtered, washed with water, and recrystallized from ethanol, yielding the title compound, m.p. 254°–255° C (dec.).

|  | % C | % H | % N | % Cl |
|---|---|---|---|---|
| cal'd: | 72.24 | 7.85 | 7.02 | 8.88 |
| found: | 72.31 | 7.82 | 7.04 | 8.94 |

EXAMPLE 6

(±)-trans-1,2,3,4,4a,8,9,14a-octahydropyrido[4',3':2,3]-indolo[1,7-ab][1]benzazepine-3-hexanol 1.5 grams (0.036 moles) of (±)-trans-1,2,3,4,4a,8,9,14a-octahydropyrido[4',3':2,3]indolo[1,7-ab][1]benzazepine-3-hexanoic acid ethyl ester dissolved in 25 ml of dry ether was added dropwise to a stirred suspension of 380 mg (0.010 moles) of lithium aluminum hydride in 50 ml of ether under a nitrogen atmosphere. The resulting mixture was then heated for 1 hour at reflux, cooled, and decomposed with 1N sodium hydroxide solution. The ether solution was decanted from the inorganic salts, dried over anhydrous potassium carbonate, and evaporated. The solid residue thus obtained was recrystallized from benzene-hexane to give the title compound as colorless plates, m.p. 101°–102.5° C.

Using the appropriate methyl or ethyl ester to prepare the corresponding primary alcohol or using the appropriate ketone to prepare the corresponding secondary alcohol, the following alcohols can be prepared in a manner similar to that described in Examples 5 and 6, above:

TABLE 4

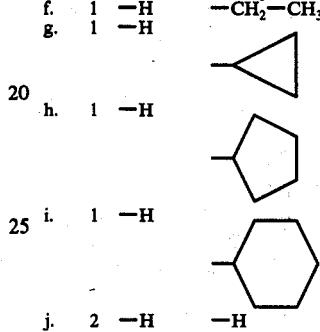

(IV) (X=CH—$R_2$)

| | n | $R_1$ | $R_2$ | m.p. | (salt) |
|---|---|---|---|---|---|
| a. | 0 | —H | —H | | |
| b. | 0 | —H | —$CH_3$ | | |
| c. | 1 | —H | —H | | |

TABLE 4-continued

| | n | $R_1$ | $R_2$ | m.p. | (salt) |
|---|---|---|---|---|---|
| d. | 1 | —$CH_3$ | —H | 143.5–145° (dec.) | — |
| e. | 1 | —H | —$CH_3$ | 238° (dec.) | (HCl) |
| f. | 1 | —H | —$CH_2$—$CH_3$ | | |
| g. | 1 | —H | cyclopropyl | | |
| h. | 1 | —H | cyclopentyl | | |
| i. | 1 | —H | cyclohexyl | | |
| j. | 2 | —H | —H | | |
| k. | 3 | —H | —H | | |
| l. | 4 | —H | —H | | |

Formulation and Use

As indicated above, the compounds of the present invention are active as CNS depressants and exhibit major tranquilizer activity which would be useful in the treatment of mental illnesses, including schizophrenia. Mental illnesses include psychoses and neuroses. The symptoms requiring treatment include anxiety, agitation, depression and hallucinations among others. The drugs used to treat psychoses include chlorpromazine and related phenothiazines, haloperidol and related butyrophenones, reserpine and related alkaloids, benzquinimide, tetrabenazine and other benzoquinolizines and chlorprothixene.

All of these drugs have side effects that limit their usefulness. The phenothiazines produce blood dyscrasias, jaundice, dermatological reactions, parkinsonism, dyskinesia and akathisia. They may also cause faintness, palpitation, nasal stuffiness, dry mouth, constipation and inhibition of ejaculations. Many of these same side effects are presented by the butyrophenones. Additional side effects are common with reserpine and similar compounds. These effects include mental depression, bradycardia, salivation, flushing, nausea and diarrhea.

There is a genuine need for psychotherapeutic agents which are effective and have fewer side effects than the drugs in use today. There is a need for such drugs which have different modes of action than the presently used drugs since none is completely effective.

The compounds of this invention can be administered in the treatment of psychiatric disorders, especially schizophrenia, according to the invention by any means that effects contact of the active ingredient compound with the site of action in the body of a warmblooded animal. For example, administration can be parenterally, i.e., subcutaneously, intravenously, intramuscularly or intraperitoneally. Alternatively or concurrently, administration can be by the oral route.

The dosage administered will be dependent upon the age, health and weight of the recipient, the type and severity of disorder, the kind of concurrent treatment, if any, frequency of treatment and the nature of the effect desired. Generally a daily dosage of active ingredient compound will be from about 0.01 to 50 mg/kg of body weight. Ordinarily, from 0.02 to 20 and preferably 0.1 to 10 mg/kg per day in one or more applications per day is effective to obtain desired results. For more potent compounds of the present invention, for example, (±)-trans-1,2,3,4,4a,8,9,14a-octahydropyrido[4′,3′:2,3]-indolo[1,7-ab][1]benzazepine-3-butyric acid, hydrochloride, the daily dosage ranges are from about 0.01 to 10 mg/kg, preferably 0.05 to 5 mg/kg and more preferably 0.1 to 2 mg/kg. For this compound, the tablet size would be about 10 mg. to be given one to four times daily.

The CNS depressant activity of the compounds of the present invention was evidenced by tests conducted in female white mice in which exploratory activity loss, blepharoptosis, catalepsy, abdominal muscle tone loss and selectively greater loss of the lift reflex than that of the grip reflex were demonstrated. All of these properties are characteristic of major tranquilizers (see R. A. Turner, "Screening Methods in Pharmacology", Academic Press, New York, 1965).

Test Descriptions

Seventeen- to 20-hour fasted female white mice, 16–20 grams each, were dosed orally with the test drug at 4, 12, 36, 108 and 324 mg/kg and were observed at 0.5, 2, 5 and 24 hours after drug administration for signs of exploratory activity loss (Explor.), blepharoptosis (Ptosis), catalepsy (Cat), abdominal muscle tone (M. Tone), lift reflex (Lift) and grip reflex (Grip).

Exploratory Activity

The mouse is placed on a stainless steel wire mesh screen (8 × 12 inches, 3 mesh per inch, ¼ inch mesh openings) "shoe-box" lid (1 inch high) and is observed for normal activities, such as nose movements, head movements with apparent visual examination of the area, and/or walking around on the screen. Normal mice respond within 2 to 3 seconds. Absence of or a marked depression of these activities for 5 seconds constitutes loss of exploratory activity.

Ptosis

The mouse is picked up by the tail and placed on the screen with its head facing the observer. Bilateral eyelid closure of 50% or more 2 seconds after placement is considered ptosis.

Catalepsy

The mouse is placed with its front paws on the edge of a stainless steel "shoe-box" cover, 1 inch high, covered with adhesive tape. Failure to remove both paws from the cover's edge within 5 seconds constitutes catalepsy.

Abdominal Muscle Tone

The observer gently strokes the abdominal musculature of the mouse with thumb and forefinger. Flaccidity (or rarely, tenseness) is recorded.

Grip and Lift Reflexes

The mouse is gently swung by the tail toward a horizontal 12-gauge wire tautly stretched 25 cm above the bench. After the mouse grasps the wire with its forepaws, its posterior end is held directly below the wire. A normal mouse grasps the wire with its forepaws and immediately lifts its hind limbs to the wire. Failure to grasp the wire with the forepaws in one of two trials constitutes loss of the *grip reflex;* failure to lift the hind limbs to grasp the wire with at least one hind paw within 5 seconds constitutes loss of the *lift reflex.*

Results

An $ED_{50}$, the calculated dose at which 50% of the mice would have responded, was calculated for each of the described parameters on each compound so tested. The $ED_{50}$'s are shown in Table 5 and may be compared to the data for a standard major tranquilizer, chlorpromazine.

TABLE 5

| Compound | Explor. | Ptosis | Cat. | M. Tone | Lift | Grip |
|---|---|---|---|---|---|---|
| Table 1, compound a. | 28.0 | 87.0 | ~100.0 | 75.0 | — | — |
| Table 2, compound b. | 8.0 | 5.0 | 14.0 | 7.0 | — | — |
| Table 1, compound c. | 28.0 | 18.0 | 56.0 | 36.0 | — | — |
| Example 2 | 37.0 | 37.0 | 178.0 | 38.0 | 224.0 | >300.0 |
| Table 3, compound b. | 11.0 | 11.0 | 37.0 | 56.0 | 71.0 | 224.0 |
| Example 3 | 4.9 | 8.7 | 22.0 | 12.0 | 56.0 | >324.0 |
| Example 4 | 6.0 | 6.0 | 6.0 | 20.0 | 20.0 | — |
| Table 4, compound e. | 5.6 | 6.0 | 5.6 | 8.0 | 12.0 | 232.0 |
| Table 2, compound e. | 23.0 | 17.0 | 15.0 | 19.0 | 78.0 | >324.0 |
| Table 3, compound d. | 50.0 | 12.0 | 50.0 | 40.0 | 62.0 | >324.0 |
| Example 5 | 0.7 | 0.4 | 1.2 | 1.2 | 5.9 | 200.0 |
| chlorpromazine | 7.0 | 7.0 | 8.0 | 8.0 | 8.0 | 240.0 |
| Table 3, compound e. | 4.0 | 4.0 | 5.6 | 5.0 | 9.7 | 200.0 |
| Example 6 | 1.5 | 2.8 | 7.0 | 4.4 | 6.2 | 200.0 |
| Table 2, compound f. | 12.0 | 20.0 | 20.0 | 7.0 | 12.0 | 300.0 |
| Table 3, compound c. | 12.0 | 20.0 | 12.0 | 12.0 | 60.0 | 200.0 |
| Table 1, compound d. | 60.0 | 100.0 | 60.0 | 60.0 | 300.0 | >324.0 |
| Table 4, compound d. | 4.5 | 7.0 | 4.5 | 4.5 | 12.0 | 260.0 |

The compounds can be formulated into compositions comprising a compound of formula IV or a pharmaceutically suitable acid-addition salt thereof together with a pharmaceutically suitable carrier. The carrier can be either a solid or liquid and the compositions can be in the form of tablets, liquid-filled capsules, dry-filled capsules, aqueous solutions, non-aqueous solutions, suppositories, syrups, suspensions and the like. The compositions can contain suitable preservatives and coloring and flavoring agents. Some examples of the carriers which can be used in the preparation of the products of this invention are gelatin capsules: sugars, such as lactose and sucrose; starches; dextrans; cellulosics, such as

13 methyl cellulose, cellulose acetate phthalate; gelatin; talc; steric acid salts; vegetable oils, such as peanut oil, cottonseed oil, sesame oil, olive oil, corn oil, and oil of theobroma; liquid petrolateum; polyethylene glycol; glycerin; sorbitol; propylene glycol; ethanol; agar; water; and isotonic saline.

In formulating the compounds, conventional practices and precautions are used. The composition intended for parenteral administration must be sterile either by using sterile ingredients and carrying out the production under aseptic conditions or by sterilizing the final composition by one of the usual procedures such as autoclaving under appropriate temperature and pressure conditions Customary care should be exercised so that no incompatible conditions exist between the active components and the diluent preservative or flavoring agent, or in the conditions employed in preparation of the compositions.

Typical formulations of the type listed above, which may be used for the administration of these compounds are:

EXAMPLE 7

Hard gelatin capsules can be prepared by filling standard two-piece hard gelatin capsules with the following mixture using conventional encapsulating equipment:

| | |
|---|---|
| Compound of Example 6 | 10 mg. |
| Lactose | 100 mg. |
| Talc | 10 mg. |
| Magnesium Stearate | 4 mg. |

EXAMPLE 8

A mixture of active drug in soy bean oil is prepared and injected by means of a positive displacement pump in gelatin to form soft gelatin capsules. A soft gelatin capsule will contain 10 mg. of active ingredient. The capsules are washed in petroleum ether and dried.

EXAMPLE 9

Tablets can be prepared by conventional procedures so that each tablet will contain:

| | |
|---|---|
| Compound of Example 5 | 10 mg. |
| Spray Dried Lactose | 125 mg. |
| Microcrystalline Cellulose | 30 mg. |
| Polyvinylpyrolidone | 3 mg. |
| Magnesium Stearate | 4 mg. |

EXAMPLE 10

An aqueous suspension for oral administration is prepared so that each 5 ml. contains:

| | | |
|---|---|---|
| Compound of Example 3 | 5 mg. | |
| Carboxy methyl cellulose | 5 % | w/v |
| Syrup | 35 % | v/v |
| Glycerin | 10 % | v/v |
| Sorbitol | 10 % | v/v |
| Methyl cellulose | 5 % | w/v |
| Sodium Benzoate | 5 mg. | |
| Butterscotch flavor | 0.1 % | v/v |
| Water Q.S. | 5 cc. | |

EXAMPLE 11

Parenteral composition suitable for intromuscular administration is prepared so that each ml. contains:

| | |
|---|---|
| Compound of Example 4 | 10 mg. |
| Polysorbate 80 | 1 mg. |
| Sodium Chloride - add enough quantity to make isotonic solution | |
| Benzyl Alcohol | 1.5 % |
| Water for Inj. Q.S. | 1 ml. |

EXAMPLE 12

A suitable number of suppositories is prepared so that each suppository contains:

| | |
|---|---|
| Table 2, compound b. | 10 mg. |
| Polyethylene Glycol 4000 | 1.5 gm. |
| Polyethylene Glycol 1000 | 1.5 gm. |

Melt the Polyethylene Glycol 4000 and Polyethylene Glycol 1000. Add the active ingredient while mixing. Pour into suppository molds and cool.

I claim:

1. A compound of the following formula:

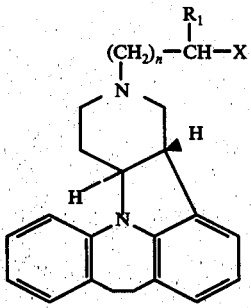

wherein

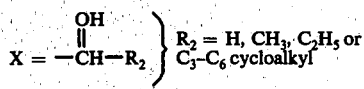

$R_2 =$ H, $CH_3$, $C_2H_5$ or $C_3$-$C_6$ cycloalkyl

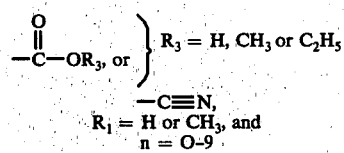

$R_3 =$ H, $CH_3$ or $C_2H_5$

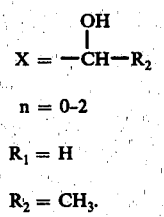

$R_1 =$ H or $CH_3$, and
$n = 0$-$9$ provided that when $R_1 =$ $CH_3$, $n = 1$, or an acid addition salt thereof with a pharmaceutically suitable acid.

2. A compound of claim 1 wherein $$X = -CH-R_2$$
with OH on CH $n = 0$-$2$ $R_1 =$ H $R_2 =$ $CH_3$.

3. A compound of claim 1 wherein

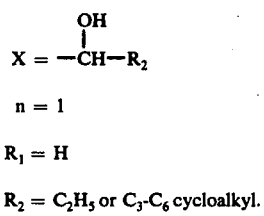

$n = 1$ $R_1 = H$ $R_2 = C_2H_5$ or $C_3$-$C_6$ cycloalkyl.

4. A compound of claim 1 wherein

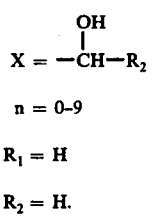

$n = 0$-$9$ $R_1 = H$ $R_2 = H$.

5. A compound of claim 1 wherein

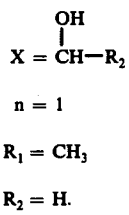

$n = 1$ $R_1 = CH_3$ $R_2 = H$.

6. A compound of claim 1 wherein
$X = -C\equiv N$
$n = 0$-$9$
$R_1 = H$.

7. A compound of claim 1 wherein
$X = -C\equiv N$
$n = 1$
$R_1 = CH_3$.

8. A compound of claim 1 wherein

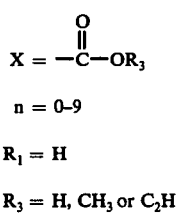

$n = 0$-$9$ $R_1 = H$ $R_3 = H, CH_3$ or $C_2H_5$.

9. A compound of claim 1 wherein

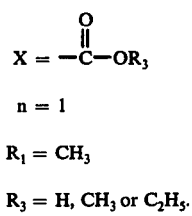

$n = 1$ $R_1 = CH_3$ $R_3 = H, CH_3$ or $C_2H_5$.

10. A pharmaceutical tranquilizing composition comprising of a pharmaceutically suitable carrier and an effective amount of a compound of claim 1.

11. A pharmaceutical tranquilizing composition comprising of a pharmaceutically suitable carrier and an effective amount of a compound of claim 2.

12. A pharmaceutical tranquilizing composition comprising of a pharmaceutically suitable carrier and an effective amount of a compound of claim 3.

13. A pharmaceutical tranquilizing composition comprising of a pharmaceutically suitable carrier and an effective amount of a compound of claim 4.

14. A pharmaceutical tranquilizing composition comprising of a pharmaceutically suitable carrier and an effective amount of a compound of claim 5.

15. A pharmaceutical tranquilizing composition comprising of a pharmaceutically suitable carrier and an effective amount of a compound of claim 6.

16. A pharmaceutical tranquilizing composition comprising of a pharmaceutically suitable carrier and an effective amount of a compound of claim 7.

17. A pharmaceutical tranquilizing composition comprising of a pharmaceutically suitable carrier and an effective amount of a compound of claim 8.

18. A pharmaceutical tranquilizing composition comprising of a pharmaceutically suitable carrier and an effective amount of a compound of claim 9.

19. A method for producing a tranquilizing effect in warm-blooded animals comprising administering to said warm-blooded animals an effective amount of a compound of claim 1.

20. A method for producing a tranquilizing effect in warm-blooded animals comprising administering to said warm-blooded animals an effective amount of a compound of claim 2.

21. A method for producing a tranquilizing effect in warm-blooded animals comprising administering to said warm-blooded animals an effective amount of a compound of claim 3.

22. A method for producing a tranquilizing effect in warm-blooded animals comprising administering to said warm-blooded animals an effective amount of a compound of claim 4.

23. A method for producing a tranquilizing effect in warm-blooded animals comprising administering to said warm-blooded animals an effective amount of a compound of claim 5.

24. A method for producing a tranquilizing effect in warm-blooded animals comprising administering to said warm-blooded animals an effective amount of a compound of claim 6.

25. A method for producing a tranquilizing effect in warm-blooded animals comprising administering to said warm-blooded animals an effective amount of a compound of claim 7.

26. A method for producing a tranquilizing effect in warm-blooded animals comprising administering to said warm-blooded animals an effective amount of a compound of claim 8.

27. A method for producing a tranquilizing effect in warm-blooded animals comprising administering to said warm-blooded animals an effective amount of a compound of claim 9.

* * * * *